US011246433B2

(12) United States Patent
Luker et al.

(10) Patent No.: US 11,246,433 B2
(45) Date of Patent: *Feb. 15, 2022

(54) RETRACTABLE SELF-CLEANING MAT

(71) Applicant: Automat Partners, LLC, Coto de Caza, CA (US)

(72) Inventors: Madison Luker, Coto de Caza, CA (US); Gerina Kim, Athens, GA (US); Alyssa Gutierrez, Athens, GA (US)

(73) Assignee: Automat Partners, LLC, Coto de Caza, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/092,823

(22) Filed: Nov. 9, 2020

(65) Prior Publication Data
US 2021/0052090 A1    Feb. 25, 2021

Related U.S. Application Data

(63) Continuation-in-part of application No. 16/839,483, filed on Apr. 3, 2020, now Pat. No. 10,827,859.
(Continued)

(51) Int. Cl.
*A47G 11/00* (2006.01)
*B65H 75/48* (2006.01)
(Continued)

(52) U.S. Cl.
CPC .............. *A47G 11/007* (2013.01); *A61L 2/10* (2013.01); *B65H 75/4471* (2013.01);
(Continued)

(58) Field of Classification Search
CPC .... A01K 29/00; A01K 1/0117; A01K 1/0135; A01K 1/0613; A47G 11/007;
(Continued)

(56) References Cited

U.S. PATENT DOCUMENTS

| 1,877,610 A | 9/1932 | Steiner |
| 1,967,422 A | 7/1934 | Nadelson |

(Continued)

OTHER PUBLICATIONS

Lloyd, J. K. F. (2017). Minimising Stress for Patients in the Veterinary Hospital: Why It Is Important and What Can Be Done about It. Veterinary Sciences, 4(2), 22. http://doi.org/10.3390/vetsci4020022.
(Continued)

*Primary Examiner* — Daniel J Rohrhoff
(74) *Attorney, Agent, or Firm* — Meunier Carlin & Curfman LLC

(57) ABSTRACT

Various implementations include an extended repeated-use table cover device. The device includes a roller, a non-silicone mat, a disinfecting enclosure, a table mount, and a winding mechanism. An outer surface of the roller is coupled to a first mat end such that rotation of the roller about a roller axis causes the mat to wind around the outer surface of the roller. An outer surface of the disinfecting enclosure defines an opening extending from the outer surface to a cavity defined by an inner surface of the disinfecting enclosure. The roller is disposed within the cavity, and the mat is extendable through the opening. The winding mechanism is for rotating the roller from an extended position to a retracted position. The mat is durable enough to be used for at least three months under expected standard use without needing to be replaced.

22 Claims, 7 Drawing Sheets

Related U.S. Application Data

(60) Provisional application No. 62/830,175, filed on Apr. 5, 2019.

(51) Int. Cl.
  *B65H 75/44* (2006.01)
  *A61L 2/10* (2006.01)

(52) U.S. Cl.
  CPC ....... *B65H 75/486* (2013.01); *B65H 2407/10* (2013.01); *B65H 2515/815* (2013.01); *B65H 2515/84* (2013.01)

(58) Field of Classification Search
  CPC ........ A47G 11/00; A47G 11/003; A47G 5/02; A61L 2/10; B65H 75/4471; B65H 75/486; B65H 2407/10; B65H 2515/815; B65H 2515/84; B65H 2301/5115; A47B 13/086; B08B 1/00; B08B 1/005; B08B 1/006; A47L 11/4083; D06G 1/00; D06B 1/12
  See application file for complete search history.

(56) References Cited

U.S. PATENT DOCUMENTS

| | | | |
|---|---|---|---|
| 4,119,991 A | 10/1978 | Martino | |
| 4,358,865 A | 11/1982 | Pagel | |
| 4,740,075 A | 4/1988 | Schoernig | |
| 5,067,546 A | 11/1991 | Jeuffray | |
| 5,718,009 A | 2/1998 | Lin | |
| 6,062,147 A | 5/2000 | Footitt | |
| 6,499,156 B1* | 12/2002 | Dirst | A61G 7/1019 5/600 |
| 7,377,490 B1 | 5/2008 | Khosravian | |
| 7,404,279 B1* | 7/2008 | Miano | A61L 2/10 53/229 |
| 7,837,077 B2 | 11/2010 | Forman | |
| 7,971,622 B2 | 7/2011 | Trionfetti | |
| 10,827,859 B2* | 11/2020 | Luker | A47G 11/007 |
| 2007/0193705 A1* | 8/2007 | Hsu | A47G 5/02 160/238 |
| 2013/0200204 A1* | 8/2013 | Hassman | B65H 16/005 242/598 |
| 2013/0239856 A1* | 9/2013 | Lee | G09F 23/08 108/50.17 |
| 2015/0344253 A1* | 12/2015 | Swami | B65H 75/28 242/532.4 |
| 2016/0007560 A1 | 1/2016 | Roofener | |
| 2017/0347619 A1* | 12/2017 | Cook | A01K 1/0135 |
| 2018/0265320 A1 | 9/2018 | Zenalden | |
| 2018/0289847 A1* | 10/2018 | McCormick | A61L 2/10 |

OTHER PUBLICATIONS

Volk, J. O., Felsted, K. E., Thomas, J. G., Siren, C. W. (2011). Executive summary of the Bayer veterinary care usage study. Journal of the American Veterinary Medical Association, 238(10):1275-82. https://www.researchgate.net/publication/51123399_Executive_summary_of_the_Bayer_veterinary_care_usage_study.

* cited by examiner

RETRACTABLE SELF-CLEANING MAT

CROSS-REFERENCE TO RELATED APPLICATIONS

This application is a continuation-in-part of U.S. application Ser. No. 16/839,483, filed Apr. 3, 2020, which claims the benefit of U.S. Provisional Patent Application No. 62/830,175, filed Apr. 5, 2019, the contents of which are incorporated herein by reference in their entirety.

BACKGROUND

Examination tables are used to support animal patients in veterinary clinics while the animals are being treated. Current veterinary examination tables pose an issue to the animal patients, clients (pet-owners), and the veterinary staff alike. Patient stress is a prevalent issue within the veterinary field, and one gaining an increasing amount of attention from professionals practicing small animal medicine. Continuing Education courses on this subject are offered nationwide, and "Fear Free" certification is on the rise for veterinary clinics.

Among the different contributors to stress within a small animal clinic are the examination tables, with research showing that approximately 80% of dogs are fearful on the examination table. Currently, the stainless-steel examination tables have low-friction surfaces, which add to the stress of visiting a veterinary clinic. This stress can have effects on the patient animal's vital signs and can cause a potential risk to veterinary staff if the stress manifests into reactionary biting and scratching by the patient animal. As a consequence, this biting and scratching creates anxiety for clients, as they witness the discomfort of their animals. According to the Bayer veterinary care usage study, a major reason for clients failing to bring their pets to the veterinary clinic is due to stress experienced by the animal and themselves.

Additionally, the veterinary staff responsible for patient restraint experience strained effort as the staff struggle to stabilize and direct a slipping animal patient. They must use a significant amount of force to support the patient so that the patient does not slide on the examination table surface. Animals with localized injuries or fractured bones must be propped up and held carefully to avoid slippage and worsening of the condition and pain, which can require multiple staff members. This additional effort to assist the patient makes it difficult for veterinarians to easily access and treat the patient.

Another issue with examination tables is that the current method of disinfection of an examination table between patients consists of manually spraying disinfectant solution and wiping down the top surface of the examination table. Spraying does not always contact the full surface area of the table due to human error. Moreover, the disinfectant solution is often wiped away before the required contact time for disinfection, which is usually defined as 5-10 minutes.

Other industries also have a need for disinfected surfaces, such as in food processing/preparation, grocery stores, wholesale corporations, agriculture, transport facilities, various medical applications, clean rooms, and laboratories. These industries often face similar issues to those discussed above with respect to the veterinary field.

Thus, a need exists for a slip-resistant examination surface that can be quickly and easily disinfected between uses.

SUMMARY

Various implementations include an extended repeated-use table cover device. Extended repeated-use means at least three months under expected standard use without needing to be replaced. The device includes a roller, a non-silicone mat, an enclosure, a table mount, and a winding mechanism.

The roller has a roller axis, a first roller end, a second roller end opposite and spaced apart from the first roller end, and an outer surface extending axially along the roller axis from the first roller end to the second roller end. The roller is rotatable about the roller axis.

The non-silicone mat has a first mat end and a second mat end opposite and spaced apart from the first mat end. The outer surface of the roller is coupled to the first mat end such that rotation of the roller about the roller axis causes the mat to wind around the outer surface of the roller.

The enclosure has an outer surface and an inner surface defining a cavity. The outer surface defines an opening extending from the outer surface to the cavity defined by the inner surface. The roller is disposed within the cavity of the enclosure and the mat is extendable through the opening. The cavity of the enclosure is fillable with a cleaning liquid.

The table mount is for coupling the enclosure to a portion of a table.

The winding mechanism is for rotating the roller from an extended position to a retracted position. A larger portion of the mat is wound around the roller outer surface in the retracted position than in the extended position. The mat is durable enough to be moved from the retracted position to the extended position, supporting a patient, and moving from the extended position to the retracted position for at least three months under expected standard use without needing to be replaced.

In some implementations, the mat is moved from the retracted position to the extended position, supports a patient, and moves from the extended position to the retracted position more than 300 uses during a three-month period under expected standard use.

In some implementations, the mat includes vinyl.

In some implementations, the enclosure includes at least one squeegee extending at least partially into the opening. The squeegee is engageable with a portion of the mat extending through the opening.

In some implementations, the winding mechanism is a spring for biasing the rotation of the roller toward the retracted position. In some implementations, the winding mechanism includes a clutch for selectively preventing the spring for biasing the rotation of the roller toward the retracted position. In some implementations, the winding mechanism is a handle for manually rotating the roller.

In some implementations, the table mount includes at least one clamp for coupling the enclosure to a portion of a table. In some implementations, the table mount includes an adhesive for coupling the enclosure to a portion of a table.

In some implementations, the table mount is a first table mount for coupling the enclosure to a first portion of a table, and the device further includes a second table mount for coupling the second mat end to a second portion of the table.

In some implementations, the second mat end includes a coupling extension, and the second table mount defines a coupling slot. The second mat end is couplable to the second table mount by disposing the coupling extension in the coupling slot.

In some implementations, the mat includes a slip-resistant material. In some implementations, the mat includes a sterilizable material.

Various other implementations include an table cover system. The system includes an examination table and an extended repeated-use table cover device. The examination table has an examination surface for supporting a patient.

Extended repeated-use means at least three months under expected standard use without needing to be replaced. The device includes a roller, a non-silicone mat, an enclosure, a table mount, and a winding mechanism.

The roller has a roller axis, a first roller end, a second roller end opposite and spaced apart from the first roller end, and an outer surface extending axially along the roller axis from the first roller end to the second roller end. The roller is rotatable about the roller axis.

The non-silicone mat has a first mat end and a second mat end opposite and spaced apart from the first mat end. The outer surface of the roller is coupled to the first mat end such that rotation of the roller about the roller axis causes the mat to wind around the outer surface of the roller.

The enclosure has an outer surface and an inner surface defining a cavity. The outer surface defines an opening extending from the outer surface to the cavity defined by the inner surface. The roller is disposed within the cavity of the enclosure and the mat is extendable through the opening. The cavity of the enclosure is fillable with a cleaning liquid.

The table mount is for coupling the enclosure to a portion of a table.

The winding mechanism is for rotating the roller from an extended position to a retracted position. A larger portion of the mat is wound around the roller outer surface in the retracted position than in the extended position. The mat is durable enough to be moved from the retracted position to the extended position, supporting a patient, and moving from the extended position to the retracted position for at least three months under expected standard use without needing to be replaced.

The mat is configured to extend over a portion of the examination surface of the examination table in the extended position.

In some implementations, the mat is moved from the retracted position to the extended position, supports a patient, and moves from the extended position to the retracted position more than 300 uses during a three-month period under expected standard use.

In some implementations, the mat includes vinyl.

In some implementations, the enclosure includes at least one squeegee extending at least partially into the opening. The squeegee is engageable with a portion of the mat extending through the opening.

In some implementations, the winding mechanism is a spring for biasing the rotation of the roller toward the retracted position. In some implementations, the winding mechanism includes a clutch for selectively preventing the spring for biasing the rotation of the roller toward the retracted position. In some implementations, the winding mechanism is a handle for manually rotating the roller.

In some implementations, the table mount includes at least one clamp for coupling the enclosure to a portion of a table. In some implementations, the table mount includes an adhesive for coupling the enclosure to a portion of a table.

In some implementations, the table mount is a first table mount for coupling the enclosure to a first portion of a table, and the device further includes a second table mount for coupling the second mat end to a second portion of the table.

In some implementations, the second mat end includes a coupling extension, and the second table mount defines a coupling slot. The second mat end is couplable to the second table mount by disposing the coupling extension in the coupling slot.

In some implementations, the mat includes a slip-resistant material. In some implementations, the mat includes a sterilizable material.

Various other implementations include an extended repeated-use table cover device. Extended repeated-use means at least three months under expected standard use without needing to be replaced. The device includes a roller, a non-silicone mat, a disinfecting enclosure, a table mount, and a winding mechanism.

The roller has a roller axis, a first roller end, a second roller end opposite and spaced apart from the first roller end, and an outer surface extending axially along the roller axis from the first roller end to the second roller end. The roller is rotatable about the roller axis.

The non-silicone mat has a first mat end and a second mat end opposite and spaced apart from the first mat end. The outer surface of the roller is coupled to the first mat end such that rotation of the roller about the roller axis causes the mat to wind around the outer surface of the roller.

The disinfecting enclosure has an outer surface and an inner surface defining a cavity. The outer surface defines an opening extending from the outer surface to the cavity defined by the inner surface. The roller is disposed within the cavity of the disinfecting enclosure and the mat is extendable through the opening.

The table mount is for coupling the disinfecting enclosure to a portion of a table.

The winding mechanism is for rotating the roller from an extended position to a retracted position. A larger portion of the mat is wound around the roller outer surface in the retracted position than in the extended position.

The mat is durable enough to be moved from the retracted position to the extended position, supporting a patient, and moving from the extended position to the retracted position for at least three months under expected standard use without needing to be replaced.

The mat is sterilized within the disinfecting enclosure as the mat moves from the extended position to the retracted position and/or from the retracted position to the extended position.

In some implementations, the disinfecting enclosure includes a UV-C light source that disinfects the mat as the mat moves from the extended position to the retracted position and/or from the retracted position to the extended position. In some implementations, the UV-C light source emits UV light having a wavelength in the range of 100-280 nm. In some implementations, the UV-C light source includes one or more light emitting diodes, pulsed xenon lamps, fluorescent and other mercury-based lamps, or any combination thereof.

In some implementations, the mat is moved from the retracted position to the extended position, supporting a patient, and moving from the extended position to the retracted position more than 300 uses during a three-month period under expected standard use.

In some implementations, the mat includes vinyl. In some implementations, the mat partially includes silicone.

In some implementations, the winding mechanism includes a spring and a clutch. The spring is for biasing the rotation of the roller toward the retracted position and the clutch is for selectively preventing the spring from rotating the roller toward the retracted position.

In some implementations, the device further includes a table mount for coupling the enclosure to a portion of a table. The table mount includes at least one clamp for coupling the enclosure to a portion of a table.

In some implementations, the device further includes a first table mount for coupling the enclosure to a first portion of a table and a second table mount for coupling the second mat end to a second portion of the table.

In some implementations, the mat includes a slip-resistant material.

In some implementations, the mat includes a sterilizable material.

Various other implementations include a table cover device. The device includes a roller, a mat, an enclosure, and a winding mechanism.

The roller has a roller axis, a first roller end, a second roller end opposite and spaced apart from the first roller end, and an outer surface extending axially along the roller axis from the first roller end to the second roller end. The roller is rotatable about the roller axis.

The mat has a first mat end and a second mat end opposite and spaced apart from the first mat end. The outer surface of the roller is coupled to the first mat end such that rotation of the roller about the roller axis causes the mat to wind around the outer surface of the roller.

The enclosure has an outer surface and an inner surface defining a cavity. The outer surface defines an opening extending from the outer surface to the cavity defined by the inner surface. The roller is disposed within the cavity of the enclosure and the mat is extendable through the opening.

The winding mechanism is for rotating the roller from an extended position to a retracted position. A larger portion of the mat is wound around the roller outer surface in the retracted position than in the extended position.

The enclosure includes a UV-C light source that disinfects the mat as the mat moves from the extended position to the retracted position and/or from the retracted position to the extended position.

In some implementations, the UV-C light source emits UV light having a wavelength in the range of 100-280 nm. In some implementations, the UV-C light source includes one or more light emitting diodes, pulsed xenon lamps, fluorescent and other mercury-based lamps, or any combination thereof.

In some implementations, the mat includes vinyl. In some implementations, the mat includes silicone.

In some implementations, the winding mechanism includes a spring and a clutch. The spring is for biasing the rotation of the roller toward the retracted position and the clutch is for selectively preventing the spring from rotating the roller toward the retracted position.

In some implementations, the device further includes a table mount for coupling the enclosure to a portion of a table. The table mount includes at least one clamp for coupling the enclosure to a portion of a table.

In some implementations, the device further includes a first table mount for coupling the enclosure to a first portion of a table and a second table mount for coupling the second mat end to a second portion of the table.

In some implementations, the mat includes a slip-resistant material.

In some implementations, the mat includes a sterilizable material.

BRIEF DESCRIPTION OF DRAWINGS

Example features and implementations are disclosed in the accompanying drawings. However, the present disclosure is not limited to the precise arrangements and instrumentalities shown.

DETAILED DESCRIPTION

Figure 1:
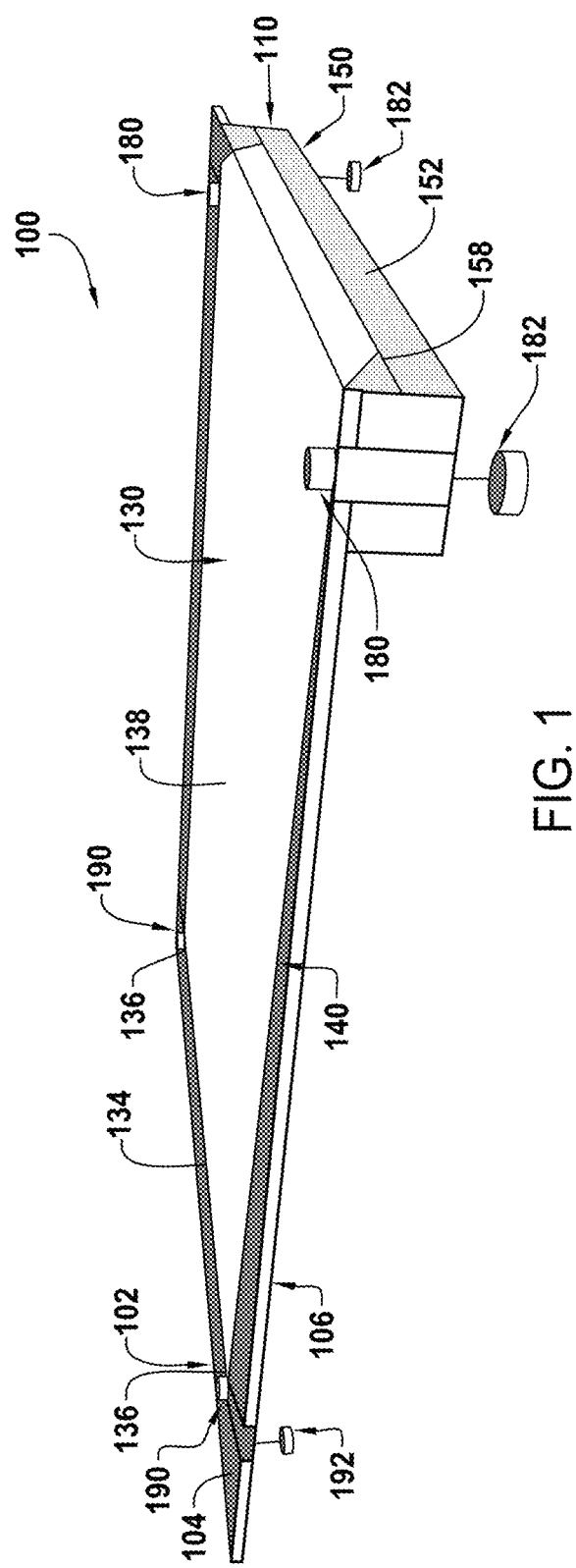
FIG. 1 is perspective view of a table cover system in which the extended repeated-use table cover device is in the extended position, according to one implementation.

The devices, systems, and methods disclosed herein provide for a retractable mat for covering a table, such as an examination table. The mat is retractable into an enclosure mounted to the table and is extendable over the top surface of the table. The mat is sterilizable and slip-resistant. When the mat is retracted into the enclosure, the mat is disinfected between uses. When used as a cover for an examination table in a veterinary application, the mat is used to support an animal. However, the devices, systems, and methods disclosed herein can be used in any other application in which a sterilizable surface is desired, such as in food processing/preparation, grocery stores, wholesale corporations, agriculture, transport facilities, various medical applications, clean rooms, and laboratories.

Various implementations include an extended repeated-use table cover device. Extended repeated-use means at least three months under expected standard use without needing to be replaced. The device includes a roller, a non-silicone mat, an enclosure, a table mount, and a winding mechanism.

The roller has a roller axis, a first roller end, a second roller end opposite and spaced apart from the first roller end, and an outer surface extending axially along the roller axis from the first roller end to the second roller end. The roller is rotatable about the roller axis.

The non-silicone mat has a first mat end and a second mat end opposite and spaced apart from the first mat end. The outer surface of the roller is coupled to the first mat end such that rotation of the roller about the roller axis causes the mat to wind around the outer surface of the roller.

The enclosure has an outer surface and an inner surface defining a cavity. The outer surface defines an opening extending from the outer surface to the cavity defined by the inner surface. The roller is disposed within the cavity of the enclosure and the mat is extendable through the opening. The cavity of the enclosure is fillable with a cleaning liquid.

The table mount is for coupling the enclosure to a portion of a table.

The winding mechanism is for rotating the roller from an extended position to a retracted position. A larger portion of the mat is wound around the roller outer surface in the retracted position than in the extended position. The mat is durable enough to be moved from the retracted position to the extended position, supporting a patient, and moving from the extended position to the retracted position for at least three months under expected standard use without needing to be replaced.

Various other implementations include a table cover system. The system includes an examination table and an extended repeated-use table cover device. The examination table has an examination surface for supporting a patient.

Extended repeated-use means at least three months under expected standard use without needing to be replaced. The device includes a roller, a non-silicone mat, an enclosure, a table mount, and a winding mechanism.

The roller has a roller axis, a first roller end, a second roller end opposite and spaced apart from the first roller end, and an outer surface extending axially along the roller axis from the first roller end to the second roller end. The roller is rotatable about the roller axis.

The non-silicone mat has a first mat end and a second mat end opposite and spaced apart from the first mat end. The outer surface of the roller is coupled to the first mat end such that rotation of the roller about the roller axis causes the mat to wind around the outer surface of the roller.

The enclosure has an outer surface and an inner surface defining a cavity. The outer surface defines an opening extending from the outer surface to the cavity defined by the inner surface. The roller is disposed within the cavity of the enclosure and the mat is extendable through the opening. The cavity of the enclosure is fillable with a cleaning liquid.

The table mount is for coupling the enclosure to a portion of a table.

The winding mechanism is for rotating the roller from an extended position to a retracted position. A larger portion of the mat is wound around the roller outer surface in the retracted position than in the extended position. The mat is durable enough to be moved from the retracted position to the extended position, supporting a patient, and moving from the extended position to the retracted position for at least three months under expected standard use without needing to be replaced.

The mat is configured to extend over a portion of the examination surface of the examination table in the extended position.

FIG. 1 shows an table cover system 100 including an examination table 102 and an extended repeated-use table cover device 110. The examination table 102 has an examination surface 104 for supporting a patient and a bottom surface 106 opposite and spaced apart from the examination surface 104. The extended repeated-use table cover device 110 includes a roller 120, a mat 130, an enclosure 150, a winding mechanism 170, a first table mount 180, and a second table mount 190. The mat 130 is extendable from the enclosure 150 to cover the examination surface 104 of the examination table 102 to provide a non-slip, subitizable, and durable surface to support an animal patient. The enclosure 150 contains a cleaning liquid 160, and when the mat 130 is retracted into the enclosure 150, the mat 130 is rolled through the cleaning liquid 160 to sanitize the mat 130. The sanitized mat 130 can then be extended from the enclosure 150 to support another patient. The mat 130 is durable enough such that the device can be used for an extended repeated use of at least three months under expected standard use without needing to be replaced.

Figure 4:
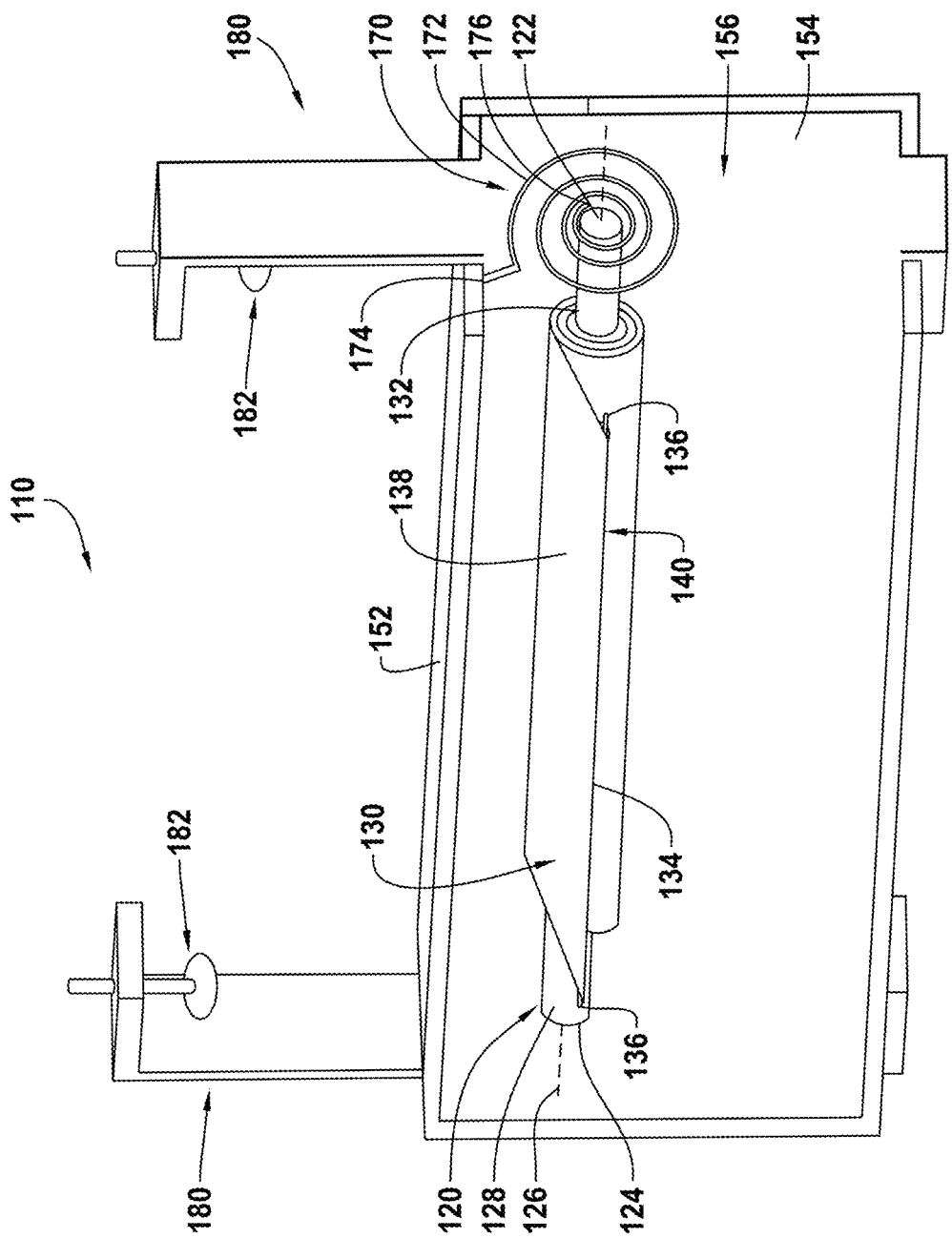
FIG. 4 is a cross-sectional view of the extended repeated-use table cover device of FIG. 3 along line A-A.
Figure 5:
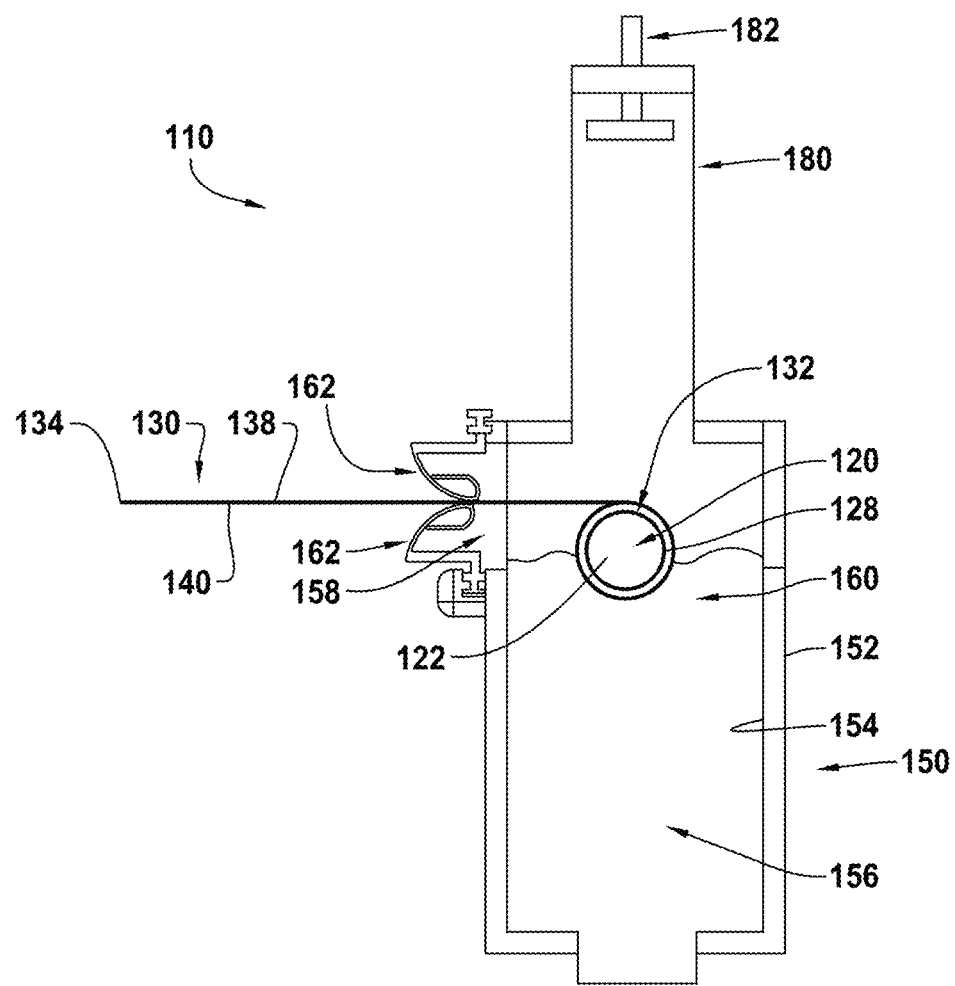
FIG. 5 is a cross-sectional view of the extended repeated-use table cover device of FIG. 3 along line B-B.

The roller 120 has a first roller end 122 and a second roller end 124 opposite and spaced apart from the first roller end 122, as shown in FIGS. 4 and 5. The roller 120 further has a roller axis 126 and an outer surface 128 extending axially along the roller axis 126 from the first roller end 122 to the second roller end 124. The roller 120 is rotatably coupled to the enclosure 150 such that the roller 120 is rotatable about the roller axis 126.

The mat 130 has a first mat end 132 and a second mat end 134 opposite and spaced apart from the first mat end 132. The first mat end 132 is coupled to the outer surface 128 of the roller 120 such that rotation of the roller 120 about the roller axis 126 causes the mat 130 to wind around the outer surface 128 of the roller 120. The second mat end 134 includes two coupling extensions 136 extending from either side of the mat 130. The coupling extensions 136 shown in FIG. 1 are ends of a bar threaded through a loop at the second mat end 134 such that the coupling extensions 136 protrude from both sides of the mat 130.

The mat 130 has a top surface 138 for supporting a patient and a bottom surface 140 for contacting the examination surface 104 of the examination table 102. The mat 130 is sized such that a portion of the mat 130 is capable of covering a veterinary examination table 102 when the mat 130 is extended from the enclosure 150, as discussed below.

The mat 130 shown in FIG. 1 is manufactured from a vinyl material. The mat 130 includes a slip-resistant top surface 138 to prevent the patient from sliding when being supported by the mat 130. The mat 130 is a sterilizable material such that the mat 130 can be cleaned when retracted into the enclosure 150, as discussed below. In some implementations, the mat is autoclavable. Although the mat 130 shown in FIG. 1 is manufactured from a vinyl material, in other implementations, the mat is manufactured out of any material durable enough to withstand being extended from the enclosure, supporting a patient, and being retracted into the enclosure for at least three months under expected standard use without needing to be replaced, as discussed below. In some implementations, the mat is manufactured from rubber. In some implementations, the mat is manufactured from multiple materials. The first mat end 132 shown in FIG. 1 is coupled to the outer surface 128 of the roller 120 by an adhesive, but in other implementations, the first mat end is coupled to the outer surface by one or more fasteners, hook and loop, compression fit in a groove defined by the outer surface, a dovetail joint, soldering, or any other coupler capable of attaching the first mat end to the outer surface with enough durability to withstand being extended from the enclosure, supporting a patient, and being retracted into the enclosure for at least three months under expected standard use without needing to be replaced.

Figure 2:
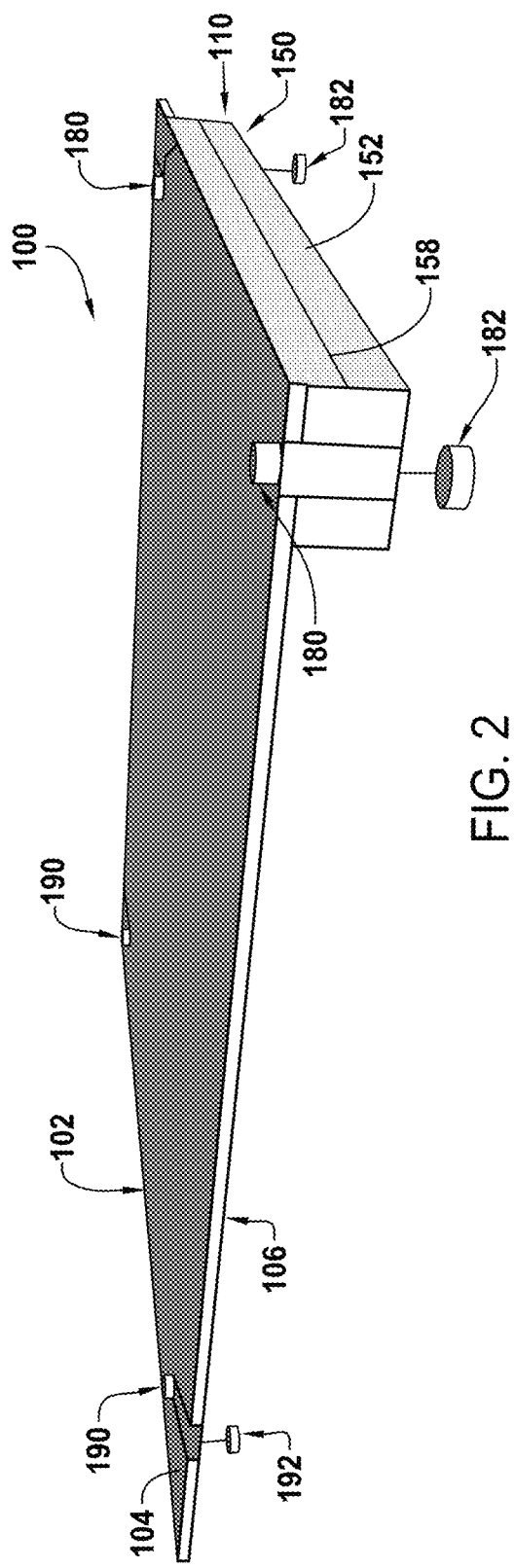
FIG. 2 is perspective view of a table cover system of FIG. 1 in which the extended repeated-use table cover device is in the retracted position.

During a three-month period of standard use, the device 110 is expected to be moved from the retracted position (shown in FIG. 2) to the extended position (shown in FIG. 1), support a patient, and moved from the extended position to the retracted position for more than 300 uses. Through experimentation, the minimum number of uses was determined to be the number of times a veterinary worker would expect the device to be able to be used before the mat 130 needed to be replaced. Thus, a mat 130 should be able to be extended from and retracted back into the device 110 more than 300 times before needing to be replaced. However, in other implementations, it may be desired for the mat to be able to be extended from and retracted back into the device more than 500 times before needing to be replaced A user of the device 110 can determine when the mat 130 or device 110 should be replaced by performing a visual inspection of the mat 130 and device 110 to determine the amount of wear of the mat 130. A mat 130 needs to be replaced when the mat 130 is found to have sufficient damage such that the mat 130 is no longer of performing its intended purpose. Such sufficient damage can include, but is not limited to, the first mat end 132 becoming irreparably uncoupled from the outer surface 128 of the roller 120, tears along the edges of the mat 130, tears that extend through the mat 130 from the top surface 138 to the bottom surface 140, and any other condition that causes the mat 130 to be incapable of being retracted, extended, or fully sterilized.

The mat 130 is also determined to be sufficiently damaged enough to need replacement when a slip-resistant mat 130 no longer has its slip-resistant property. Some damage to the mat 130 is expected and tolerable such that replacement of the mat 130 is not needed, such as, small punctures through the mat 130 from the top surface 138 to the bottom surface 140, sterilizable stains on the top surface 138 or the bottom surface 140 of the mat 130, minor tears on the mat 130 which do not extend from the top surface 138 to the bottom surface 140, or any other damage that does not affect the retraction, extension, sterilizability, or slip-resistant properties of the mat 130.

As used herein, the terms "sterilize" and "disinfect" refer to cleaning an area and do not necessarily require the killing of 100% of the microorganisms in the area.

In some implementations, the mat is manufactured from any non-silicone material. The term "non-silicone," as used throughout this application, means that the material is not 100% silicone but could be partially made of silicone or could contain no silicone. Thus, a non-silicone mat does not comprise 100% silicone material but could comprise some silicone along with another material or could comprise no silicone. Through experimentation, it was determined that silicone, by itself, is not a durable enough material for a mat 130 designed for extended repeat use for at least three months without needing to be replaced. A mat manufactured of only silicone tears and punctures too easily, and must be replaced too often, to be suitable for use as a cover for a veterinary examination table for three months under expected standard use. It is acknowledged, however, that in some circumstances, a mat would not need to be durable enough to be repeatedly used for at least three months under expected standard use without needing to be replaced. In some implementations, the mat is durable enough to be moved from the retracted position to the extended position, supporting a patient, and moving from the extended position to the retracted position for less than three months under expected standard use without needing to be replaced. In implementations designed for such circumstances, the mat can be manufactured from any material, including silicone.

Figure 3:
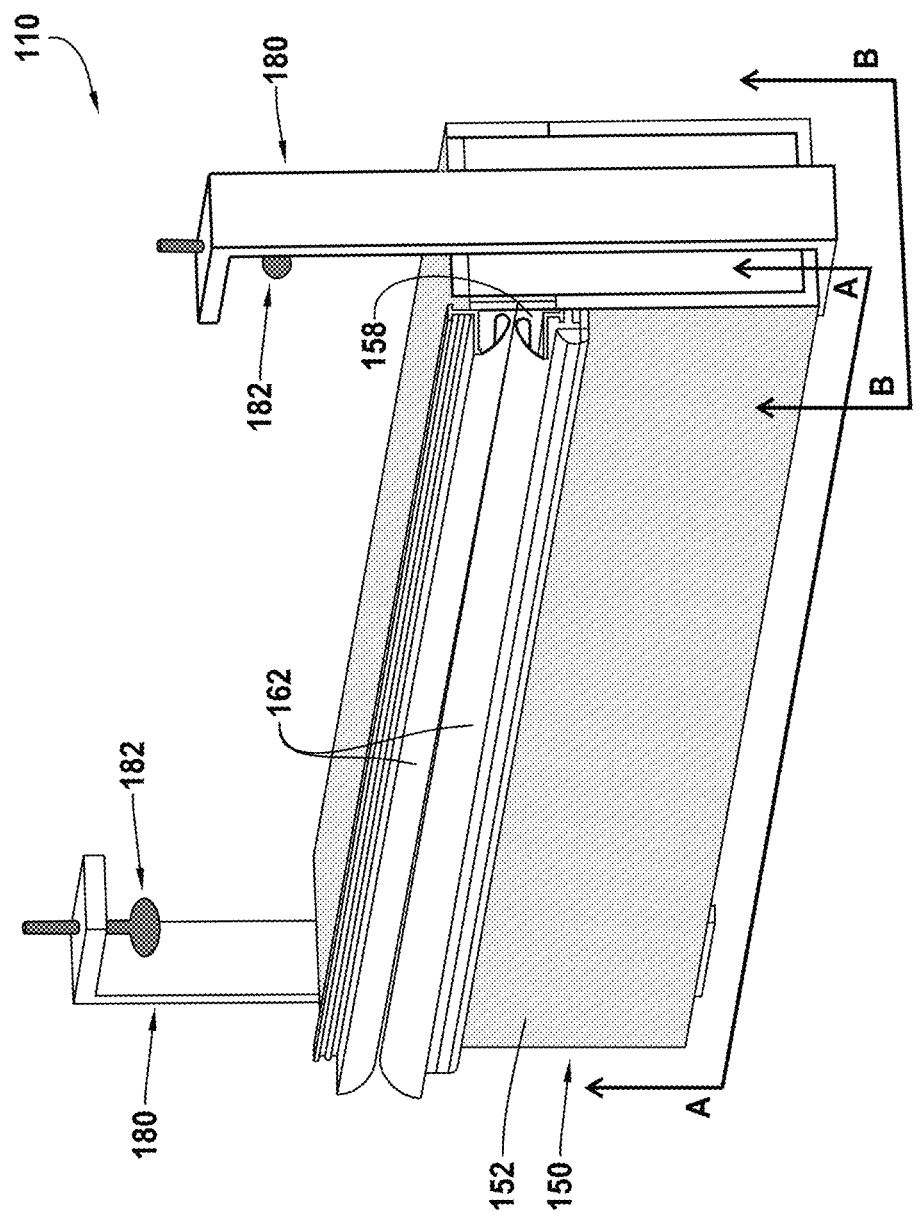
FIG. 3 is perspective view of the opening of the enclosure of the extended repeated-use table cover device of FIG. 1.

The enclosure 150 is a hollow container sized for enclosing the roller 120 and the portion of the mat 130 extending around the roller 120, as shown in FIGS. 3-5. The enclosure 150 has an outer surface 152 and an inner surface 154. The inner surface 154 defines a cavity 156 in which the roller 120 and a portion of the mat 130 are enclosed. An opening 158 is defined by the outer surface 152 of the enclosure 150 and extends from the outer surface 152 to the inner surface 154. The opening 158 is sized such that the mat 130 is extendable from within the cavity 156, through the opening 158. The cavity 156 of the enclosure 150 is sealed to hold liquid such that the cavity 156 is fillable with a cleaning liquid 160. When the mat 130 is retracted by winding the mat 130 around the roller 120, a portion of the mat 130 is submerged in the cleaning liquid 160.

As shown in FIG. 3, the enclosure 150 includes two squeegees 162 coupled to the opening 158 that extend partially into the opening 158. The two squeegees 158 are coupled to opposite sides of the opening 158 such that one squeegee 162 engages a portion of the top surface 138 of the mat 130 and the other squeegee 162 engages a portion of the bottom surface 140 of the mat 130 when the mat 130 extends through the opening 158. The squeegees 162 are long enough so that each squeegee 162 engages the entire width of the mat 130. When the mat 130 is extended through the opening 158 of the enclosure 150, the squeegees 162 remove excess cleaning liquid 160 from the surfaces 138, 140 of the mat 130 such that the mat 130 is dry, or can quickly dry, before a patient is placed on the mat 130. Although the device 110 shown in FIG. 3 includes two squeegees 162, in other implementations, the device includes no squeegees, one squeegee, or more than two squeegees.

The winding mechanism 170 shown in FIG. 4 is enclosed in the enclosure 150. The winding mechanism 170 is used to rotate the roller 120 about the roller axis 126, which causes the mat 130 to wind around the outer surface 128 of the roller 120. As the mat 130 winds around the roller 120, the mat 130 moves from an extended position (shown in FIG. 1) to a retracted position (shown in FIG. 2), in which a larger portion of the mat 130 is wound around the outer surface 128 or the roller 120 in the retracted position than in the extended position. Thus, the winding of the mat 130 retracts the mat 130 into the enclosure 150.

The winding mechanism 170 shown in FIG. 4 is a clock-type spring 172 having a first end 174 and a second end 176. The first end 174 of the spring 172 is coupled to a portion of the enclosure 150, and the second end 176 of the spring 172 is coupled to the roller 120 and rotates with the roller 120. The spring 172 is configured to bias the rotation of the roller 120 toward the retracted position. Thus, when the mat 130 is moved from the retracted position (FIG. 2) to the extended position (FIG. 1), tension is put on the spring 172 to urge the roller 120 to rotate and cause the mat 130 to be wound back to the retracted position.

Figure 7:
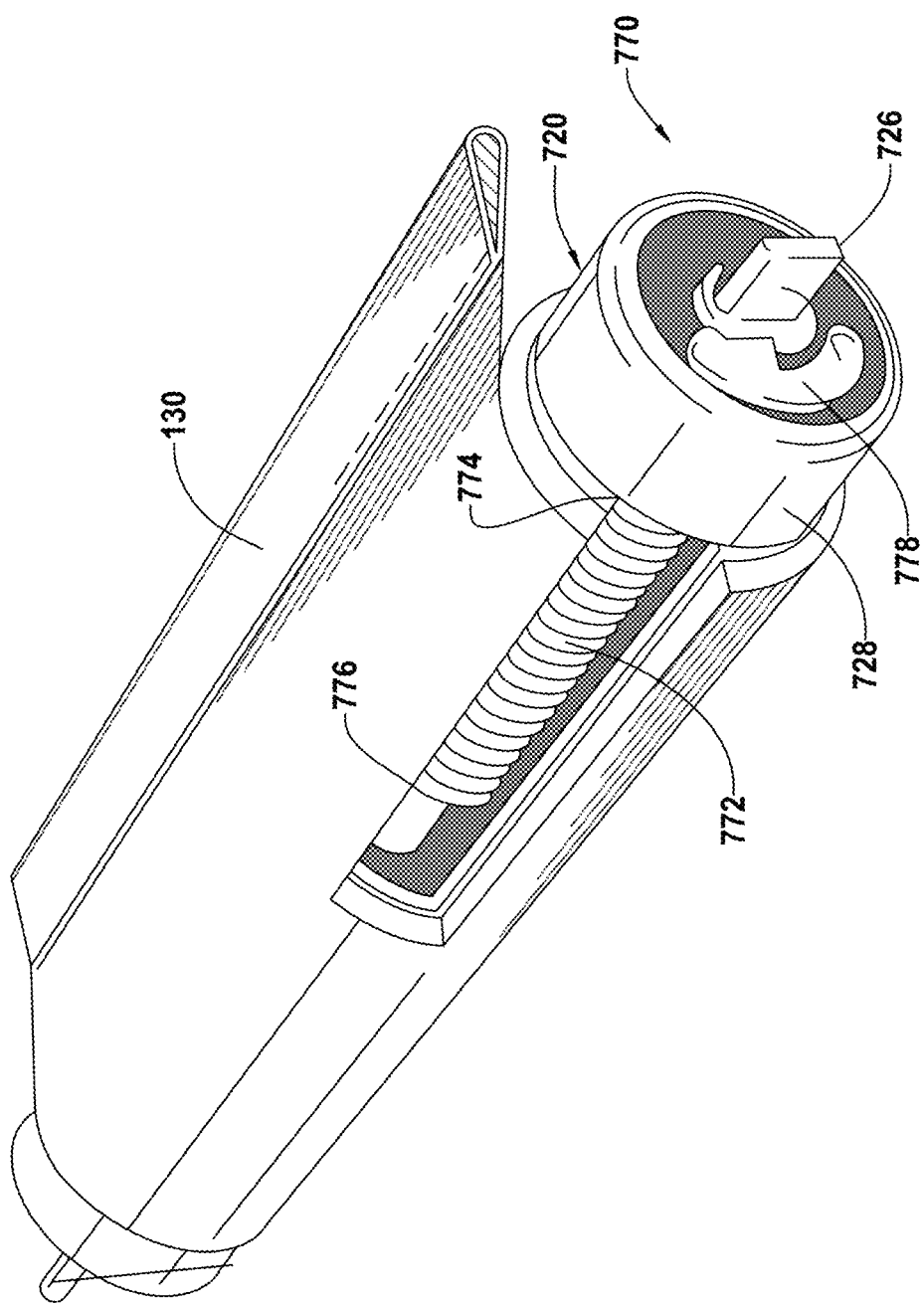
FIG. 7 is a perspective view of a winding mechanism of an extended repeated-use table cover device, according to another implementation.

FIG. 7 shows another implementation of a winding mechanism 770. The winding mechanism 770 is used to rotate the roller 720 about the roller axle 726, which causes the mat 130 to wind around the outer surface 728 of the roller 720. As the mat 130 winds around the roller 720, the mat 130 moves from an extended position (shown in FIG. 1) to a retracted position (shown in FIG. 2), in which a larger portion of the mat 130 is wound around the outer surface 728 or the roller 720 in the retracted position than in the extended position. Thus, the winding of the mat 130 retracts the mat 130 into the enclosure 150.

The winding mechanism 770 shown in FIG. 7 is a torsion spring 772 having a first end 774 and a second end 776. The first end 774 of the spring 772 is coupled to a clutch 778, and the second end 776 of the spring 772 is coupled to the roller axle 726 and rotates with the roller axle 726. The clutch 778 is coupled to the roller axle 726 and the roller 720. The spring 772 is configured to bias the rotation of the roller 720 toward the retracted position. When the mat 130 is initially moved from the retracted position (FIG. 2) to the extended position (FIG. 1), tension is put on the spring 772 to urge the roller 720 to rotate back to the retracted position. However, the clutch 778 prevents the spring 772 from causing the roller 720 to rotate relative to the roller axle 726, causing the mat 130 to remain in the extended position. While the mat 130 is in the extended position, causing the roller 720 to rotate further in the extended position direction releases the clutch 778 and allows the roller 720 to rotate relative to the roller axle 726, and the tension of the spring 772 causes the roller 720 to rotate and cause the mat 130 to be wound back to the retracted position.

Although the winding mechanisms 170, 770 shown in FIGS. 4 and 7 are springs 172, 772, in other implementations, the winding mechanism is an electric motor that rotates the roller toward the extended position and/or toward the retracted position when activated. The winding mechanism includes controls for activating the electric motor to rotate the roller toward the extended position and/or toward the retracted position. In some implementations, the winding mechanism is a crank handle coupled to an end of the roller such that manual rotation of the handle rotates the roller toward the retracted position.

The first table mount 180 is used to couple the enclosure 150 to a portion of the examination table 102. The enclosure 150 shown in FIG. 1 is configured to be coupled to the bottom surface 106 of the examination table 102 adjacent an end of the examination table 102. The first table mount 180 includes two clamps 182 that can be tightened for gripping the examination surface 104 and bottom surface 106 of the examination table 102 such that the enclosure 150 is disposed below the examination table 102. The device 110 can be uncoupled from the examination table 102 by loosening the clamps 182. Although the first table mount 180 shown in FIG. 1 includes two clamps 182, in some implementations, the first table mount includes a single clamp or more than two clamps. In some implementations, the first table mount includes an adhesive or fasteners for coupling the enclosure to the examination table. In some implementations, the first table mount is configured to mount the enclosure to the examination surface or an end of the examination table. In some implementations, the device includes a wall mount rather than a first table mount, and the wall mount uses clamps, adhesive, or fasteners to couple the enclosure to a wall adjacent the examination table. In some implementations, the device does not include a first table mount and the enclosure is coupled to the examination table.

Figure 6:
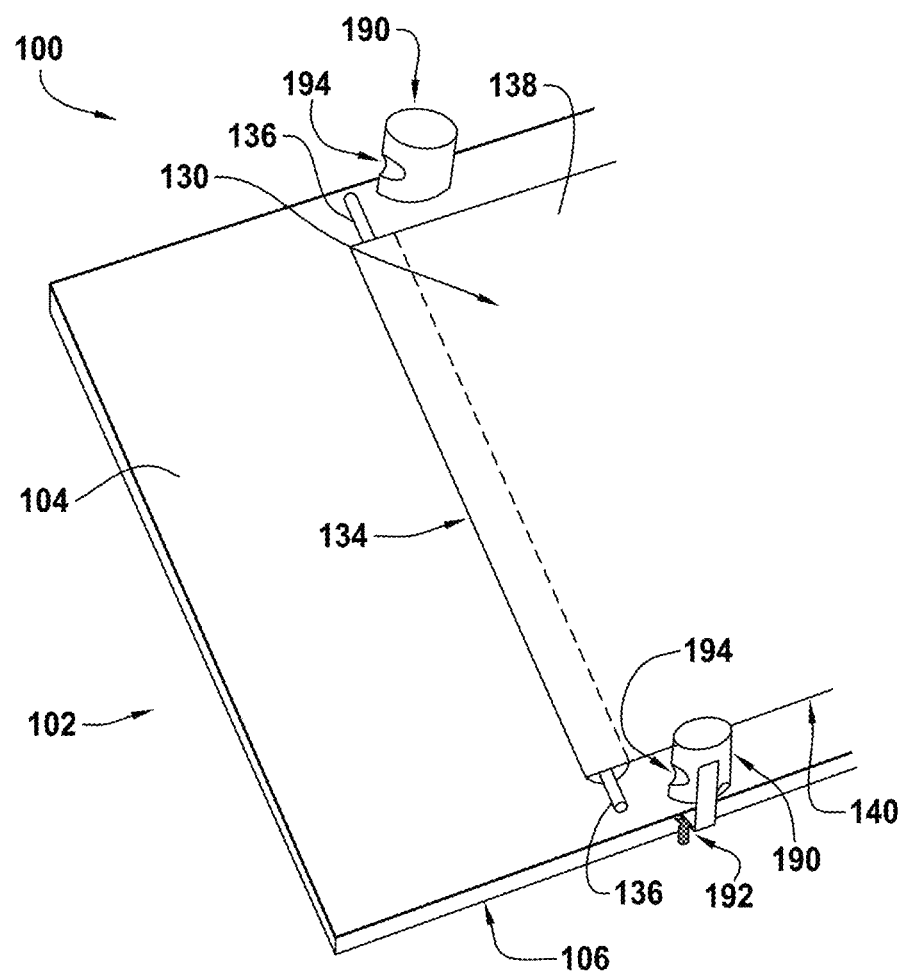
FIG. 6 is a perspective view of the second table mount of the table cover system of FIG. 1.

FIG. 6 shows the second table mount 190. The second table mount 190 is used to couple the second mat end 134 to the examination table 102 when the roller 120 is in the extended position. The second table mount 190 includes two clamps 192 that can be tightened for gripping the examination surface 104 and bottom surface 106 of the examination table 102. The second table mount 190 also includes two coupling slots 194 for accepting each of the two coupling extensions 136 at the second mat end 134. When the mat 130 is moved to the extended position with the second table mount 190 coupled to a portion of the examination table 102, disposing the coupling extensions 136 within the coupling slots 194 prevents the winding mechanism 170, 770 from urging the mat 130 toward the retracted position. Although the second table mount 190 shown in FIG. 1 includes coupling slots 194 for coupling the second mat end 134, in other implementations, the second table mount includes a second set of clamps, fasteners, hooks, adhesive, hook and loop, or any other coupler for coupling the second table mount to the second mat end capable of securing the second mat end while supporting a patient. In some implementations, the device does not include second table mounts.

Figure 8:
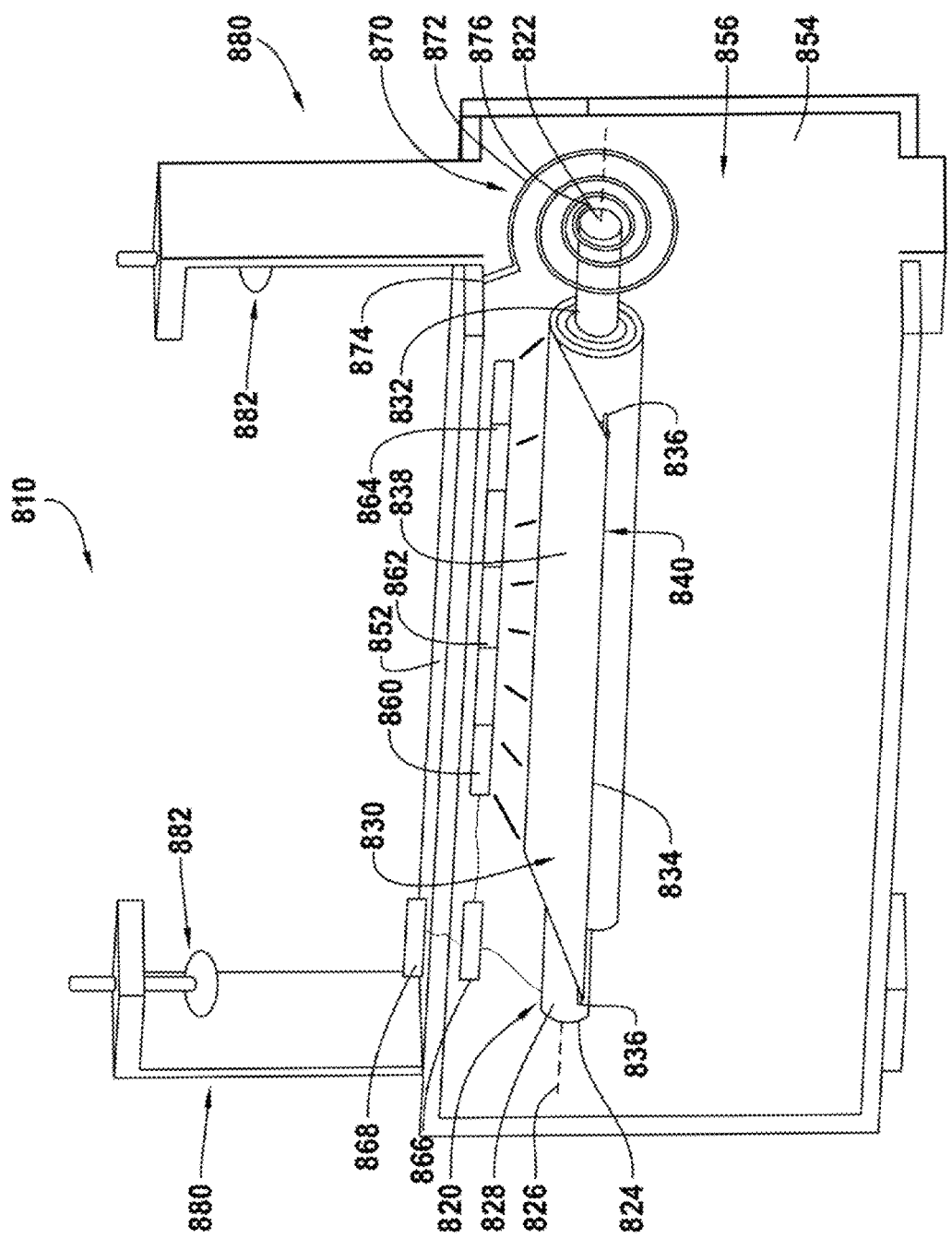
FIG. 8 is a perspective view of a table covering device according to another implementation.

FIG. 8 shows a table cover device according to another implementation. Features of the device shown in FIG. 8 that are similar to the features shown in FIGS. 1-7 are labeled with similar reference numbers.

The device 800 in FIG. 8 is similar to the devices 100 shown in FIGS. 1-7, except that the device 800 shown in FIG. 8 does not include a sealed enclosure 150 for holding a cleaning liquid 160 or squeegees 162. Instead, the device 800 shown in FIG. 8 includes a disinfecting enclosure 850 that includes a UV-C light source 860. The UV-C light source 860 is disposed within the cavity 856 of the enclosure 850 and is positioned to emit UV-C light directed toward the roller 820 and/or the portion of the mat 830 disposed within the enclosure 850. As the mat 830 moves from the extended position to the retracted position, and/or from the retracted position to the extended position, the UV-C light source 860 emits UV-C light to sterilize the mat 830.

The UV-C light source 860 shown in FIG. 8 includes a light bar 862 of light emitting diodes 864 that are configured to emit UV light having a wavelength in the range of 100-280 nm. This range of UV light wavelength is capable of destroying nucleic acids and disrupting the DNA of microorganisms, which can kill or inactivate microorganisms such as bacteria, viruses, molds, and other pathogens.

The device 800 can also include a switch 866 that activates and deactivates the UV-C light source 860 and a power source 868 for providing electrical power to the UV-C light source 860. The switch 866 can be any type of switch, such as a manual toggle switch, a motion activated switch that is activated by the movement of the mat, or a switch that is activated by the rotation of the roller. The power source 868 can be a portable power source such as a battery or the device could include a power cord for electrically coupling the UV-C light source to an electrical outlet.

Although the device 800 shown in FIG. 8 includes a light bar 862 of UV-C light emitting diodes 864, in other implementations, the light source can include any device that is capable of emitting UV-C light within a range that is capable of killing or inactivating microorganisms, such as low-pressure mercury-vapor lamps, excimer lamps, or pulsed xenon lamps. In some implementations, the UV-C light source includes any number of one or more lights. In some implementations, the UV-C light source is not disposed within or is only partially disposed within the enclosure. In some implementations, the range or wavelengths emitted by the UV-C light source includes any range capable of killing or inactivating microorganisms, such as the wavelength ranges for UV-B and UV-A light. In some implementations, the device includes two or more UV-C light sources. In some implementations, the device includes only one of, or a combination of, a cleaning liquid, a UV-C light source, and/or any other disinfecting device.

In some implementations, the UV-C light can be included in any portion of the device such as within the roller, exterior to the disinfecting enclosure, or anywhere in which the mat can be sterilized within the disinfecting enclosure as the mat moves from the extended position to the retracted position and/or from the retracted position to the extended position.

A number of example implementations are provided herein. However, it is understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. An extended repeated-use table cover device, wherein extended repeated-use means at least three months under expected standard use without needing to be replaced, the device comprising:
   a roller having a roller axis, a first roller end, a second roller end opposite and spaced apart from the first roller end, and an outer surface extending axially along the roller axis from the first roller end to the second roller end, the roller being rotatable about the roller axis;
   a non-silicone mat having a first mat end and a second mat end opposite and spaced apart from the first mat end, wherein the outer surface of the roller is coupled to the first mat end such that rotation of the roller about the roller axis causes the mat to wind around the outer surface of the roller;
   a disinfecting enclosure having an outer surface and an inner surface defining a cavity, the outer surface defining an opening extending from the outer surface to the cavity defined by the inner surface, wherein the roller is disposed within the cavity of the disinfecting enclosure and the mat is extendable through the opening;
   a table mount for coupling the disinfecting enclosure to a portion of a table; and
   a winding mechanism for rotating the roller from an extended position to a retracted position, wherein a larger portion of the mat is wound around the roller outer surface in the retracted position than in the extended position,
   wherein the mat is durable enough to be moved from the retracted position to the extended position, supporting a patient, and moving from the extended position to the retracted position for at least three months under expected standard use without needing to be replaced,
   wherein the mat is sterilized within the disinfecting enclosure as the mat moves from the extended position to the retracted position and/or from the retracted position to the extended position.

2. The device of claim 1, wherein the disinfecting enclosure includes a UV-C light source that disinfects the mat as the mat moves from the extended position to the retracted position and/or from the retracted position to the extended position.

3. The device of claim 2, wherein the UV-C light source emits UV light having a wavelength in the range of 100-280 nm.

4. The device of claim 2, wherein the UV-C light source comprises one or more light emitting diodes, pulsed xenon lamps, fluorescent and other mercury-based lamps, or any combination thereof.

5. The device of claim 1, wherein the mat is moved from the retracted position to the extended position, supporting a patient, and moving from the extended position to the retracted position more than 300 uses during a three-month period under expected standard use.

6. The device of claim 1, wherein the mat comprises vinyl.

7. The device of claim 1, wherein the mat partially comprises silicone.

8. The device of claim 1, wherein the winding mechanism includes a spring and a clutch, the spring for biasing the rotation of the roller toward the retracted position and the clutch for selectively preventing the spring from rotating the roller toward the retracted position.

9. The device of claim 1, wherein the table mount comprises at least one clamp for coupling the enclosure to a portion of a table.

10. The device of claim 1, wherein the table mount is a first table mount for coupling the disinfecting enclosure to a first portion of a table, wherein the device further comprises a second table mount for coupling the second mat end to a second portion of the table.

11. The device of claim 1, wherein the mat comprises a slip-resistant material.

12. The device of claim 1, wherein the mat comprises a sterilizable material.

13. A table cover device, the device comprising:
   a roller having a roller axis, a first roller end, a second roller end opposite and spaced apart from the first roller end, and an outer surface extending axially along the roller axis from the first roller end to the second roller end, the roller being rotatable about the roller axis;
   a mat having a first mat end and a second mat end opposite and spaced apart from the first mat end, wherein the outer surface of the roller is coupled to the first mat end such that rotation of the roller about the roller axis causes the mat to wind around the outer surface of the roller;
   an enclosure having an outer surface and an inner surface defining a cavity, the outer surface defining an opening extending from the outer surface to the cavity defined by the inner surface, wherein the roller is disposed within the cavity of the enclosure and the mat is extendable through the opening; and
   a winding mechanism for rotating the roller from an extended position to a retracted position, wherein a larger portion of the mat is wound around the roller outer surface in the retracted position than in the extended position,
   wherein the enclosure includes a UV-C light source that disinfects the mat as the mat moves from the extended position to the retracted position and/or from the retracted position to the extended position.

14. The device of claim 13, wherein the UV-C light source emits UV light having a wavelength in the range of 100-280 nm.

15. The device of claim 13, wherein the UV-C light source comprises one or more light emitting diodes, pulsed xenon lamps, fluorescent and other mercury-based lamps, or any combination thereof.

16. The device of claim 13, wherein the mat comprises vinyl.

17. The device of claim 13, wherein the mat comprises silicone.

18. The device of claim 13, wherein the winding mechanism includes a spring and a clutch, the spring for biasing the rotation of the roller toward the retracted position and the clutch for selectively preventing the spring from rotating the roller toward the retracted position.

19. The device of claim 13, further comprising a table mount for coupling the enclosure to a portion of a table, wherein the table mount comprises at least one clamp for coupling the enclosure to a portion of a table.

20. The device of claim 13, further comprising a first table mount for coupling the enclosure to a first portion of a table and a second table mount for coupling the second mat end to a second portion of the table.

21. The device of claim 13, wherein the mat comprises a slip-resistant material.

22. The device of claim 13, wherein the mat comprises a sterilizable material.

* * * * *